United States Patent [19]

Bivins

[11] 4,275,490
[45] Jun. 30, 1981

[54] METHOD AND APPARATUS FOR SECURING CALVARIUM SKULL SECTION TO BASAL SKULL SECTION

[76] Inventor: Charles F. Bivins, Rte. 1, Box 278, Burlington, N.C. 27215

[21] Appl. No.: 25,290

[22] Filed: Mar. 28, 1979

Related U.S. Application Data

[63] Continuation-in-part of Ser. No. 963,815, Nov. 27, 1978, abandoned.

[51] Int. Cl.³ ............................................. A01N 1/00
[52] U.S. Cl. ..................................... 27/21; 128/92 B
[58] Field of Search ............... 27/21; 128/92 R, 92 A, 128/92 B, 92 BC, 303 R, 337, 335; 35/17

[56] References Cited

U.S. PATENT DOCUMENTS

| 2,839,815 | 6/1958 | Reeves et al. ........................... 27/21 |
| 3,220,081 | 11/1965 | Rector ................................. 128/92 R |

FOREIGN PATENT DOCUMENTS

| 1240313 | 7/1960 | France ................................. 128/92 A |
| 304941 | 7/1971 | U.S.S.R. .............................. 128/92 BC |

Primary Examiner—John D. Yasko
Attorney, Agent, or Firm—Mills & Coats

[57] ABSTRACT

The present invention relates to a method and apparatus for firmly securing a formerly cut and removed cranial cap skull section to the base portion of the cranium, after the cranial cap skull section has been cut and removed in the course of an autopsy. To accomplish this, a frictional plug or hook assembly is anchored in the cervical foramen cavity extending downwardly from the base of the skull, and another anchoring assembly is secured to the removed cranial cap skull section. A flexible coupler in the form of an elastomer is operatively attached between said frictional plug or hook assembly and said anchoring assembly anchored in said cranial cap skull section so as to hold with a tensional force the cranial cap skull section firmly in place about the cranium thereby effectively completing the calvarium closure.

13 Claims, 7 Drawing Figures

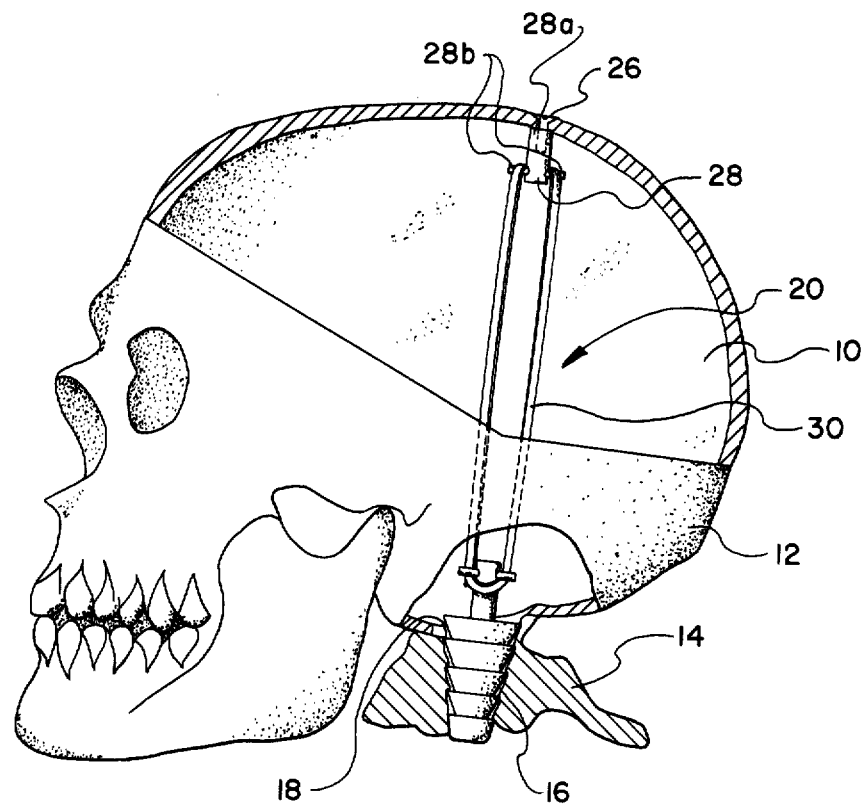
FIG. 1
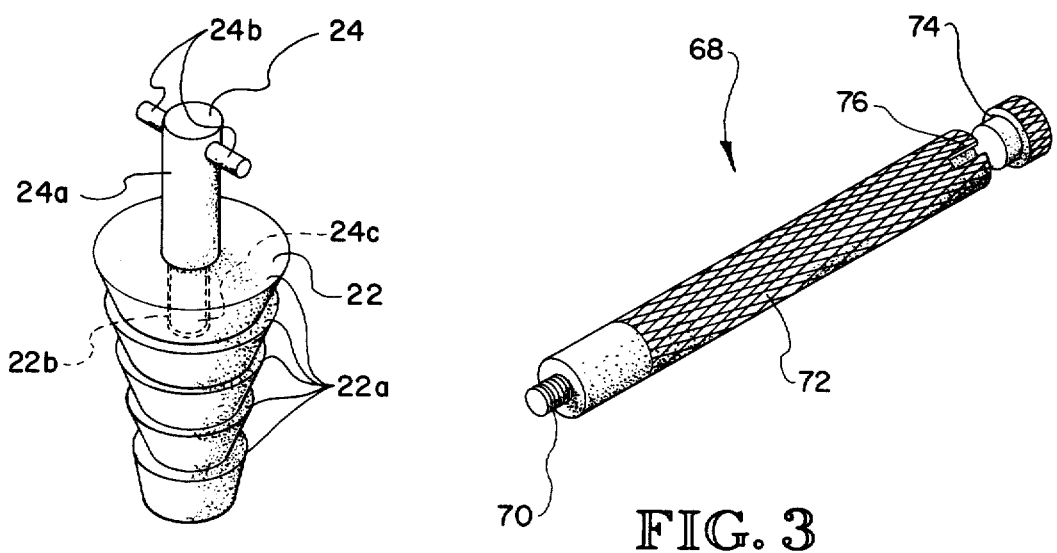
FIG. 2
FIG. 3

METHOD AND APPARATUS FOR SECURING CALVARIUM SKULL SECTION TO BASAL SKULL SECTION

This is a continuation-in-part of U.S. patent application Ser. No. 963,815, filed Nov. 27, 1978, now abandoned.

The present invention relates to the mortuary art, and more particularly to a method and means for securing a calvarium skull section to the basal skull section after a top section of the skull has been cut and removed in the course of an autopsy in order that access may be gained to the brain and other internal skull areas.

BACKGROUND OF INVENTION

In performing an autopsy, a top portion of the skull, which for reference purpose herein is referred to as a cranial cap skull section or calvarium skull section, is cut and removed from the basal skull (or base of the cranium) in order that access can be gained to the brain and any other internal area of the skull.

After the autopsy is performed, the corpse is taken by an undertaker who then has to prepare the corpse for the funeral. It then becomes the responsibility of the undertaker to resecure the cut and removed cranial cap skull section to the basal skull section, and this obviously is a very important responsibility where the corpse is going to be viewed by family, friends, acquaintances, and others.

In the past, various means have been employed to resecure a cut cranial cap skull section to the basal skull section after an autopsy has been performed. For example, one approach that has been followed in the past entails drilling tiny holes in and through the skull above and below the saw kerf, and then inserting and manipulating tiny wires through the holes and then tying the wire outside of the skull such that the wire couples the cranial cap section to the basal skull section. This method is not satisfactory from a cosmetic consideration because of the presence of the wire outside of the skull and below the skin is difficult to hide and camouflage and often distracts from the physical appearance of the corpse.

Other approaches to coupling a removed cranial cap skull section to the basal skull section have been tried. For example, the disclosures in the following U.S. Patents deal with this problem: U.S. Pat. Nos. 3,205,553; 2,839,815; and 3,220,081.

In U.S. Pat. No. 3,205,553 and U.S. Pat. No. 2,839,815, both disclosures suggest extending a coupling member such as a fastening strap or bracket across the saw kerf formed about the skull, and then to fasten the particular coupling member about the external areas of the skull. As with the use of wire, such devices cannot be completely hidden and often one can see bulges formed under the skin caused by the presence of such coupling members being present about the external area of the skull, and this again often severely affects the physical appearance of the corpse.

An internal coupling method is disclosed in U.S. Pat. No. 3,220,081, wherein this disclosure suggests the use of a calvarium clip disposed internally across the saw kerf. The problem with this method is that it is often unworkable, besides being very difficult to properly implement. Moreover, after placement, the cranial cap skull section is often not really firmly secured, and is proned to slip and slide away from its proper position of fit.

SUMMARY OF INVENTION

The present invention provides a method and apparatus for providing a calvarium closure that is designed to overcome the problems of the prior art, and particularly those problems generally described above. More particularly, as contrasted to exterior skull coupling devices of the prior art, the method and apparatus of the present invention provides an internal coupling device that lies internally of the outer skull surface, and which, therefore, does not create bulges and disfigurations about the outer surface of the skull about the saw kerf.

The method and apparatus of the present invention entails anchoring a frictional plug or hook assembly in the cervical foramen below the base of the skull, and also anchoring a second anchoring stud assembly in the cut and removed cranial cap skull section. Then an elastomer coupler, such as a rubber band or surgical tube, is operatively interconnected between said frictional plug or hook assembly and said second anchoring stud assembly so as to exert a pulling action therebetween which is effective to hold the cranial cap skull section in a firmly set and secured position about the basal skull section.

It is, therefore, an object of the present invention to provide a new and improved method and apparatus for forming a calvarium closure after an autopsy.

Another object of the present invention is to provide a method and means for forming a calvarium closure that is reliable, inexpensive, simple, and convenient and relatively easy to implement.

Still a further object of the present invention is to provide a method and coupling apparatus for forming a calvarium closure after an autopsy that is effective to secure a cut and removed cranial cap skull section to the basal skull in such a fashion that the skull autopsy operation and effects thereof are not visibly detectable.

It is also an object of the present invention to provide a connecting or coupling assembly for securing the cranial cap skull section to said basal skull section that is operative to firmly and securely hold and retain the cranial cap skull section about the basal skull just as if the two skull sections had never been separated.

Finally, it is an object of the present invention to provide a flexible coupling device for securing the cranial cap skull section to said basal skull section that can be readily adjusted for any size skull, thereby not requiring certain size and length components for certain size skulls.

Other objects and advantages of the present invention will become apparent from a study of the following description and the accompanying drawings which are merely illustrative of the present invention.

BRIEF DESCRIPTION OF THE DRAWINGS

FIG. 1 is a side elevational view, partially in section, illustrating the calvarium closure connecting device of the present invention.

FIG. 2 is a perspective view of an anchoring means employed within the cervical foramen and which forms a part of the calvarium closure device of the present invention.

FIG. 3 is a perspective view of an insertion-boring tool that is utilized in performing the calvarium closure suggested by the method of the present invention.

THE CALVARIUM CLOSURE DEVICE

Figure 4:
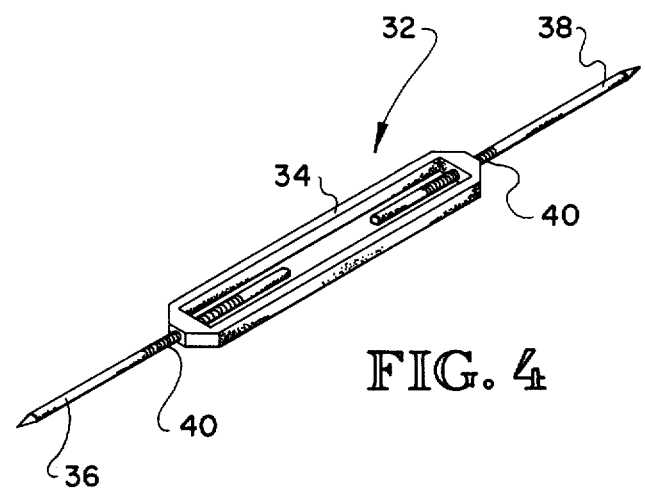
FIGS. 4 and 5 are views of alternate cranial cap section anchoring means.

For purposes of reference in this disclosure, the skull will be referred to as being comprised of two basic parts—one part being the top portion of the skull removed during autopsy and which is referred to as a cranial cap skull section or calvarium skull section 10, and a second part of the skull remaining after the removal of the cranial cap skull section 10 which is referred to as the basal skull section 12. At the base of the skull there is a bone that is referred to as the first cervical vertebra 14 and formed therein is a cervical foramen cavity 16. An opening about the base of the skull that leads into the cervical foramen cavity 16 is referred to as the foramen magnum.

Turning to the drawings, and particularly FIG. 1, the calvarium closure device of the present invention is shown therein, indicated generally by the numeral 20, coupled or connected generally between the cranial cap skull section 10 and the basal skull section 12. Viewing the calvarium closure device 20 in more detail, it is seen that the same includes a frictional plug 22 that is constructed of plastic or any other suitable material and which is adapted to be anchored within the cervical foramen cavity 16. Frictional plug 22 includes a series of axially spaced circumference ribs 22a that increase in diameter from the lower portion thereof toward the top. Formed about the top of the frictional plug 22 and extending downwardly therein is a threaded bore 22b.

Associated with and attached to the frictional plug 22 is a coupler attaching means 24 that includes a shaft 24a, a threaded shaft extension 24c that is adapted to be threaded into the threaded bore 22b of the frictional plug 22. In addition, coupler attaching means 24 includes a pair of pin studs or dogs 24b that project outwardly therefrom about the top portion, as illustrated in FIGS. 1 and 2.

Continuing to refer to the calvarium closure device 20 of the present invention, a second anchoring means or anchoring assembly is provided about the cranial cap skull section 10. This second anchoring means includes a screw (or holding member) 26 that is inserted through an opening formed in the cranial cap skull section 10. A second coupler attaching means 28 that includes a hollow threaded shaft 28a is secured to screw 26 by screwing the threaded hollow shaft 28a onto the screw 26. In addition, like the coupler attaching means 24 of FIG. 2, the coupler attaching means 28 includes a pair of pin studs or dogs 28b that project outwardly at one end thereof.

Interconnected between the respective coupler attaching means 24 and 28, is an elastomer coupler 30, such as a rubber band. In the case of the illustration in FIG. 1, one end of the elastomer coupler is wound around the pin studs 28b of the second coupler attaching means 28, while another portion of the elastomer coupler 30 is wrapped around the first coupler attaching means 24 such that the pin studs 24b thereof retain and hold the elastomer coupler. Consequently, it is appreciated that for a selected elastomer coupler 30, that when retained between the respective coupler attaching means 24 and 28, that the elastomer coupler 30 exerts a tension force that tends to pull the cranial cap skull section 10 firmly against the basal skull section 12 in such a fashion that the two skull sections are retained together in a coupled or secured relationship.

Turning to FIG. 4, there is shown therein an alternate anchoring means or assembly for the second anchoring means disposed about the cranial cap section 10 of the skull. This alternate anchoring means or assembly is referred to as an adjustable turn buckle-spike coupler and is indicated by the numeral 32. Viewing this device in more detail, it is seen that the same comprises a turn buckle 34 having two spikes 36 and 38 with appropriate threads 40 provided thereon and contained within opposite ends of the turn buckle 34. It is appreciated that the effective span of the turn buckle-spike coupler 32 can be adjusted by screwing the spikes outwardly or inwardly with respect to the turn buckle 34 so as to extend across the interior concave side of the cranial cap skull section 10. It is appreciated that the ends of the respective spikes would be adjusted to where the spike ends actually embed into the wall structure of the cranial cap skull section. For attaching the elastomer coupler 30, the turn buckle 34 could be provided with a hook or other appropriate type of retaining means.

Figure 5:
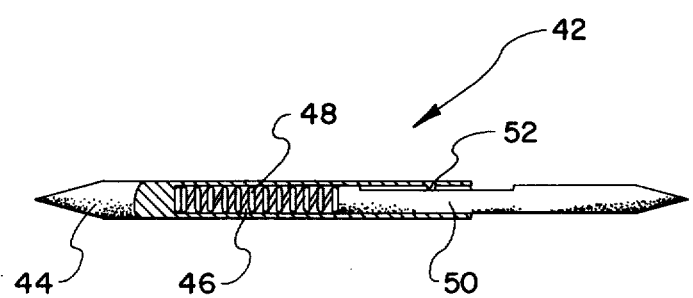

In FIG. 5, another alternative design for the second anchoring means is disclosed. In this alternate design, there is shown a spring loaded telescopically contained spike mechanism indicated generally by the numeral 42. This device includes a spike section 44 that includes a spike end and a hollow opening 46 that receives a portion of a telecopically contained spike 50. A spring 48 is provided within the hollow opening 46 and is contained therein adjacent the inner end of spike section 50, thereby exerting an outward force against the spike section 50. The telescopically contained spike section 50 is retained within the hollow opening 46 of spike section 44 by the provision of a stop device indicated by the numeral 52.

Figure 6:
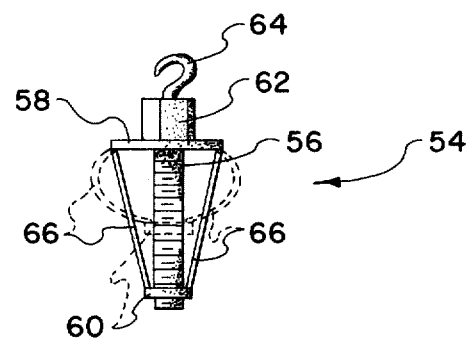
FIG. 6 is an alternate design for the anchoring assembly illustrated in FIG. 2.

In FIG. 6, there is disclosed an alternate design for the anchoring means illustrated in FIG. 2. More particularly, in FIG. 6, there is disclosed an anchoring stud assembly indicated generally by the numeral 54 that comprises a threaded shaft 56 rotatively threaded within a top plate 58 and a nut 60. A turning head 62 is secured to the top of the threaded shaft and a hook 64 extends upwardly therefrom for receiving the elastomer coupler 30. A plurality of flexible anchoring bellows 66 are interconnected between top plate 58 and nut 60. Consequently, as the threaded shaft 56 is turned, the distance between the nut 60 and top plate 58 decreases, causing the flexible anchoring bellows 66 to project outwardly from the threaded shaft 56, as indicated in dotted lines in FIG. 6, so as to anchor the entire anchoring stud assembly 54 in place. It is appreciated that such an alternate design could be used as the anchoring means within the cervical foramen cavity 16, as illustrated in FIG. 1.

Figure 8:
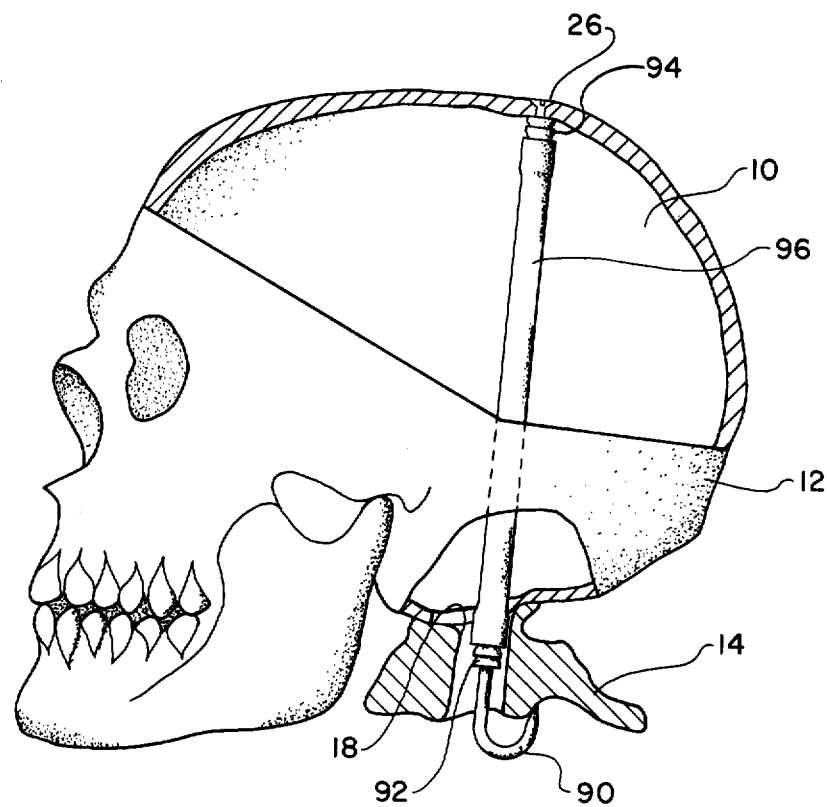
FIG. 8 is a side elevational view similar to FIG. 6 illustrating yet another embodiment of the calvarium closure device of the present invention.

With reference to FIG. 8, another alternative embodiment for the calvarium closure is shown therein. In this embodiment, a hook assembly is anchored about the cervical foramen cavity extending downwardly from the base of the skull, the hook assembly being generally referred to as a first anchoring means to be anchored about an area that generally lies about the lower area of the basal skull section. The hook assembly comprises a threaded hook 90 that is inserted within the cervical foramen cavity and in the process of achieving an anchored position the hook end is urged through the soft tissue lying between the first and second vertebrae (in this illustrated embodiment) such that the hook 90 can be firmly anchored as illustrated in FIG. 8. It should be pointed out that hook 90 could be manipulated through soft tissue between the basal skull section and the first vertebra in order to achieve a firmly secured anchored position.

As noted above, the end of the hook opposite the hook end is threaded and includes a stretch tubing coupler end portion 92 threaded thereon. The stretch tubing coupler 92 is of the conventional rubber tube type coupler that is adapted to receive one end of rubber or surgical type tubing therearound and to securely hold the same thereabout once the end is properly stretched over the coupler.

Screw 26 appropriately placed in the cranial skull section as already discussed hereinabove and is also threaded to receive a second stretch tubing coupler 94. To complete the calvarium closure, an elastomer 96 in the form of a rubber, surgical type tubing section, such is operatively coupled with each of the couplers 92 and 94. Then, in a manner similar to that already described, the cranium skull section is positioned and manipulated into a secure position about the basal skull section, thereby completing the calvarium closure.

METHOD OF FORMING CALVARIUM CLOSURE

Before proceeding with a step-by-step discussion of the method of forming the calvarium closure of the present invention, attention is directed to FIG. 3, and the disclosure therein of an insertion-boring tool, indicated generally by the numeral 68. This tool is particularly useful in practicing the method of the present invention, and in viewing the same it is seen that it includes a threaded extension shaft 70, a main body portion 72, a dual notched turning end 76 and a detachable anvil 74.

First, in performing the method of forming a calvarium closure according to the present invention, the frictional plug 22 is threaded onto the threaded extension shaft 70 of the insertion-boring tool 68. The anvil 74 is also inserted onto the appropriate end of the insertion-boring tool 68. Then with the cranial cap section 10 completely removed from the basal skull section 12, the frictional plug 22 is inserted through the foramen magnum of the cranium into the posterior cervical foramen of the atlas and is secured therein by driving the insertion-boring tool 68 with a hammer. Once the frictional plug 22 is securely anchored within the cervical foramen cavity 16, the insertion-boring tool 68 is appropriately turned such that the threaded extension shaft 70 thereof is unscrewed from the threaded bore 22b of the frictional plug 22.

After this, the first coupler attaching means 24 can be secured to the frictional plug 22 by threading the shaft extension 24c into the threaded bore 22b of the frictional plug.

Now to anchor the second anchoring means or anchoring assembly within the interior or concave side of the cranial cap skull section 10, the cranial cap skull section is placed on a solid block with the convex side down such that the top of the skull will be positioned face down. A drill can then be attached to the insertion-boring tool 68 or a drill associated with a conventional hand or electric drill can be utilized to drill a hole through the cranial cap skull section 10 with it being understood that the hole should be generally aligned with the already anchored frictional plug 22 when the cranial cap skull is properly in place about the basal skull section. The drill hole is not countersunken from the inside, but the cranial cap skull section is turned over, that is with the convex side up and then in a careful and gentle manner the drilled hole is countersunken from the top just enough for the screw head 26 to set flush within the drilled hole.

Screw 26 is then placed through the drilled and countersunken hole formed in the cranial cap skull section, as illustrated in FIG. 1, and then the pin studs 28b of the coupler attaching means 28 is inserted into the dual notches of the notched end 76 of the insertion-boring tool 68. After this, with the use of the insertion-boring tool 68, the second coupler attaching means 28 is threaded, from inside of the cranial cap skull section 10, onto the projecting portion of screw 26. Thus, this completes the anchoring of the second anchoring means about the cranial cap skull section 10.

Then the cranial cap skull section is placed over the base portion of the cranium, and one side is raised so that with the hand the elastomer coupler 30 can be properly positioned about the respective coupler attaching means 24 and 28. As illustrated in FIG. 1, for best results the elastomer coupler 30 should be retained about opposite sides of the respective coupler attaching means 24 and 28. If the particular elastomer coupler 30 is too long, a knot can be tied about an intermediate portion thereof prior to placement around the respective coupler attaching means, so as to insure sufficient tension such that the elastomer coupler 30 exerts a sufficient pulling force on the cranial cap skull section so as to hold the same firmly in place, without the same being prone to slip and slide away from its appropriate fit.

Figure 7:
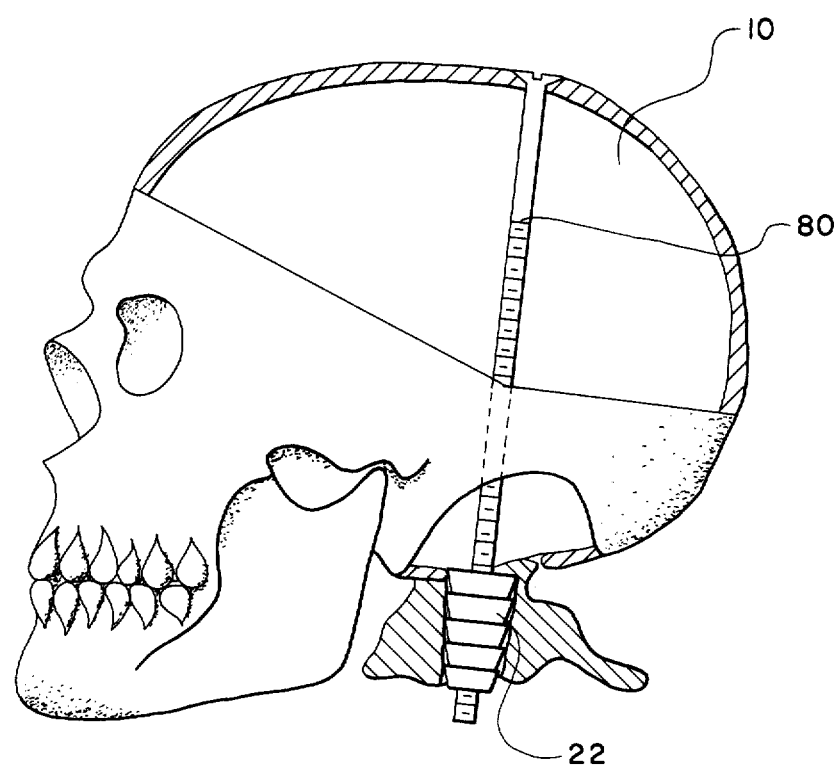
FIG. 7 is a side elevational view similar to FIG. 1, illustrating another embodiment of the calvarium closure device of the present invention.

Finally in FIG. 7 another alternate calvarium assembly design is shown. In this embodiment, the frictional plug 22 includes a threaded bore completely through the plug, and the frictional plug is inserted the same as described for the other embodiments disclosed herein. A flexible screw 80 constructed of nylon or lexan, or other suitable material is inserted through the cranial cap skull section 10, and appropriately countersunken. The lower remote end of screw 80 is threaded into and through the frictional plug 22, as illustrated in FIG. 7. The bore in the cranial skull section for receiving screw 80 is aligned as best possible with the frictional plug 22. But because the screw 80 is excessively long and is flexible, it is appreciated that alignment does not have to be precise.

With respect to FIG. 8, the basic method of forming the calvarium closure with this embodiment is substantially as described hereinabove. The basic difference lies in securing stretch tubing coupler 94 onto screw 96, and appropriately anchoring hook 90 in an area that generally lies about the lower area of the basal skull section. In this regard, it is understood that hook 90 includes stretch tubing coupler 92 and that the respective stretch tubing couplers 92 and 94 are effectively interconnected by an elastomer member 96 in the form of a section of conventional surgical tubing as the respective ends thereof are stretched over a portion of the couplers 92 and 94.

Therefore, it is appreciated that the entire calvarium closure device of the present invention lies interiorly of the outside of the corpse's skull, and consequently, the problems associated with the prior art devices that lie outside of the skull do not exist. More particularly, the coupling device employed with this present invention exerts a very sufficient and positive force that assures a very secure and firm fit between the two skull sections involved and once the coupling has been completed, one cannot visually detect that a portion of the skull has been removed from the corpse during the course of an autopsy.

Consequently, it is appreciated that the present invention, both the method and coupling apparatus, substantially improves over the prior art and presents a more effective and efficient means for calvarium closure.

The terms "upper", "lower", "forward", rearward", etc., have been used herein merely for the convenience of the foregoing specification and in the appended claims to describe the method and apparatus for securing a calvarium skull section to the basal skull section and its parts as oriented in the drawings. It is to be understood, however, that these terms are in no way limiting to the invention since the method and apparatus may obviously be practical in many different positions when in actual use.

The present invention, of course, may be carried out in other specific ways than those herein set forth without departing from the spirit and essential characteristics of the invention. The present embodiments are therefore, to be considered in all respects as illustrative and not restrictive, and all changes coming within the meaning and equivalency range of the appended claims are intended to be embraced herein.

What is claimed is:

1. A calvarium assembly for securing a calvarium skull section to the basal skull section after the calvarium skull section has been cut and removed from the skull as a part of an autopsy, said calvarium connecting assembly comprising: first anchoring means for forming a first anchor point about an area that generally lies about the lower area of said basal skull section; second anchoring means for forming a second anchor point within said calvarium skull section in general alignment with said first anchoring means; coupler attaching means associated with both said first and second anchoring means for allowing said first and second anchoring means to be interconnected; and flexible coupling means operatively interconnected between said coupler attaching means associated with said first and second anchoring means for securing said calvarium skull section to said basal skull section with a biasing type holding action as said flexible coupling means tends to exert a pulling action between said first and second anchoring means so as to firmly and securely hold said calvarium skull section securely in place about said basal skull section.

2. The calvarium connecting assembly of claim 1 wherein said first anchoring means includes a frictional anchoring plug adapted to be securely anchored in the cervical foramen cavity that extends generally downwardly from the base area of said basal skull section.

3. The calvarium connecting assembly of claim 2 wherein said flexible coupling means comprises an elastomer adapted to be connected at one end to said coupler attaching means associated with said frictional anchoring plug and at an opposite end to said coupler attaching means associated with said second anchoring means, whereby said elastomer exerts a tension force between said frictional anchoring plug and said second anchoring means so as to hold said calvarium skull section securely in place about said basal skull section.

4. The calvarium connecting assembly of claim 3 wherein said second anchoring means includes a threaded holding member secured through the cranial cap of said calvarium skull section and projecting inwardly about the concave side of said calvarium skull section.

5. The calvarium connecting assembly of claim 4 wherein said coupler attaching means associated with said second anchoring means comprising a hollow threaded shaft and a plurality of stud pins projecting therefrom, wherein said hollow threaded shaft is adapted to be secured in a threaded fashion to said threaded holding member of said second anchoring means and wherein said stud pins of said coupler attaching means are operative to retain a portion of said elastomer extending between said first and second anchoring means.

6. The calvarium connecting assembly of claim 1 wherein said second anchoring means normally associated with said calvarium skull section comprises an adjustable turn buckle-spike assembly having two oppositely projecting spikes threadedly supported about opposite ends of a turn buckle, whereby said spikes may be expanded across the concave side of said calvarium skull section and embedded about the cranial cap thereof so as to provide said second anchoring means about the calvarium skull section for attaching said flexible coupling means thereto.

7. The calvarium connecting assembly of claim 1 wherein said second anchoring means includes a pair of oppositely projecting anchoring spikes telescopically contained within a housing and spring biased for outward movement.

8. The calvarium connecting assembly of claim 1 wherein said first anchoring means includes a stud assembly having a threaded shaft and bellow anchoring means disposed thereabout for moving outwardly and engaging surrounding body portions in response to said shaft being turned, so as to anchor the entire stud assembly.

9. A method of performing a calvarium closure wherein in the course of an autopsy a top section of the skull, referred to as a calvarium skull section, is cut and removed from the basal skull section, said method of performing the calvarium closure comprising the steps of: anchoring a first anchoring means within the cervical foramen cavity that extends generally adjacent the lower area of the basal skull section; anchoring a second anchoring means to the formerly cut and removed calvarium skull section in alignment with said first anchoring means such that said second anchoring means generally projects from the concave side of said calvarium skull section; and attaching one portion of an elastomer coupler to one of said anchoring means and stretching the elastomer coupler and attaching another portion thereof to said other anchoring means so as to pull said calvarium skull section into a firmly fitting securely held appropriate position about said basal skull section to form the calvarium closure.

10. The method of claim 9 wherein anchoring said second anchoring means within said calvarium skull section comprises: drilling a hole through the cranial cap of said calvarium skull section, countersinking the drilled hole about the outer convex surface of said calvarium skull section, and inserting into said drilled hole a threaded holding member which forms a part of said second anchoring means.

11. A calvarium assembly for securing a calvarium skull section to the basal skull section after the calvarium skull section has been cut and removed from the skull as a part of an autopsy, said calvarium connecting assembly comprising: anchoring means adapted to be positioned and anchored about an area that generally lies about the lower area of said basal skull section; threaded bore means associated with said anchoring means; and an elongated flexible threaded screw inserted through said calvarium skull section and extending downwardly therefrom towards said anchoring means where a threaded end portion of said flexible screw is screwed into said threaded bore means associated with said anchoring means for securing said calvarium skull section to said basal skull section with a holding action as said flexible screw and anchoring means holds said calvarium skull section securely in place about said basal skull section.

12. The calvarium connecting assembly of claim 1 wherein said first anchoring means includes a hook assembly adapted to be anchored about an area that generally lies about the lower area of said basal skull section.

13. The calvarium connecting assembly of claim 1 wherein said first anchoring means includes a hook assembly having a hook member and a stretch tubing coupler secured thereto; and wherein said second anchoring means includes a second stretch tubing coupler; and wherein said flexible coupling means includes a section of elastic tubing having two ends with each of said ends being stretched over and around a portion of the respective stretch tubing couplers so as to effectively couple said first and second anchoring means for securing said calvarium skull section to said basal skull section.

* * * * *